US00RE50117E

(19) United States
(12) Reissued Patent
Hughes et al.

(10) Patent Number: US RE50,117 E
(45) Date of Reissued Patent: Sep. 10, 2024

(54) SYSTEM AND METHOD FOR PROVIDING MULTI-LAYERED ACCESS CONTROL

(71) Applicant: IQVIA Inc., Durham, NC (US)

(72) Inventors: Benjamin Alexander Hughes, London (GB); Michael Carl Friedrich Opel, Croydon (GB); Braley B. Crandall, Los Angeles, CA (US)

(73) Assignee: IQVIA Inc., Durham, NC (US)

(21) Appl. No.: 17/875,868

(22) Filed: Jul. 28, 2022

Related U.S. Patent Documents

Reissue of:
(64) Patent No.: 10,726,148
Issued: Jul. 28, 2020
Appl. No.: 14/830,220
Filed: Aug. 19, 2015

(51) Int. Cl.
*G06F 21/62* (2013.01)
*G16H 10/60* (2018.01)
*H04L 9/40* (2022.01)

(52) U.S. Cl.
CPC ..... *G06F 21/6227* (2013.01); *G06F 21/6245* (2013.01); *G16H 10/60* (2018.01); *H04L 63/102* (2013.01); *H04L 63/105* (2013.01); *G06F 2221/032* (2013.01); *G06F 2221/2141* (2013.01)

(58) Field of Classification Search
CPC ..... G16H 10/60; H04L 63/102; H04L 63/105; G06F 21/6227; G06F 21/6245; G06F 2221/2141; G06F 2221/032
See application file for complete search history.

(56) References Cited

U.S. PATENT DOCUMENTS 6,408,336 B1 * 6/2002 Schneider ..... H04L 63/0218 709/229
6,785,728 B1 * 8/2004 Schneider ..... H04L 63/0218 709/229
7,143,051 B1 * 11/2006 Hanby ..... G06Q 10/10 705/4

(Continued)

OTHER PUBLICATIONS

Extended European Search Report dated Jan. 19, 2017, European patent application No. 16184681.1, IMS Health Incorporated, 7 pages.

(Continued)

*Primary Examiner* — Jalatee Worjloh
(74) *Attorney, Agent, or Firm* — John Maldjian, Esq.; David L. D'Amato, Esq.; Stevens & Lee PC

(57) ABSTRACT

A method and system to provide multi-layered access control for healthcare datasets are disclosed. The method comprises defining an information policy for each of healthcare datasets, wherein the information policy comprises information access permissions. Further, an organization policy is defined for each of the healthcare datasets, wherein the organization policy comprises license permissions for organizations accessing the healthcare datasets. Thereafter, a user account master policy is defined for each of the healthcare datasets, wherein the user account master policy comprises account permissions assigned to users of the organizations. Subsequently, a master user policy is generated for each of the users based on the information policy, the organization policy, the user account master policy, or a combination thereof, wherein the master user policy comprises access control permissions to provide each of the users access to the healthcare datasets.

20 Claims, 8 Drawing Sheets

(56) References Cited

U.S. PATENT DOCUMENTS 7,272,625 B1 * 9/2007 Hannel ..... H04L 63/04 709/200
7,822,065 B2 * 10/2010 Lu ..... H04W 88/02 370/328
7,912,856 B2 * 3/2011 Hannel ..... H04L 63/0272 707/781
8,136,143 B2 * 3/2012 Hannel ..... H04L 63/0218 370/252
8,635,686 B2 * 1/2014 Sriram ..... H04L 63/102 726/12
8,745,384 B2 * 6/2014 Persaud ..... G06F 21/606 713/165
8,965,921 B2 * 2/2015 Gajic ..... G06F 17/30286 707/770
9,727,590 B2 * 8/2017 Gajic ..... G06F 17/30289
9,882,767 B1 * 1/2018 Foxhoven ..... H04L 61/4552
9,916,475 B2 * 3/2018 Enck ..... G06F 21/629
9,948,655 B1 * 4/2018 Gerweck ..... G06F 16/22
10,237,303 B2 * 3/2019 Simone, Jr. ..... H04L 63/145
10,530,779 B1 * 1/2020 Gerweck ..... G06F 21/00
2002/0103811 A1 * 8/2002 Fankhauser ..... G16H 40/67
2004/0250122 A1 * 12/2004 Newton ..... H04L 63/1425 726/2
2005/0236474 A1 10/2005 Onuma et al.
2006/0047752 A1 * 3/2006 Hornby ..... G06F 21/6227 709/205
2006/0161791 A1 * 7/2006 Bennett ..... G06F 12/1408 713/193
2008/0010233 A1 * 1/2008 Sack ..... G06F 21/6227
2008/0195843 A1 * 8/2008 Muniandy ..... G06T 15/005 712/31
2008/0295146 A1 * 11/2008 Sriram ..... H04L 63/102 726/1
2008/0313712 A1 * 12/2008 Ellison ..... H04L 63/101 726/4
2009/0234850 A1 * 9/2009 Kocsis ..... G06F 16/213
2009/0254392 A1 * 10/2009 Zander ..... G06F 21/6218 705/50
2010/0154024 A1 * 6/2010 Boxmeyer ..... G06F 21/85 726/1
2011/0302310 A1 * 12/2011 Diachina ..... H04L 63/0263 709/225
2012/0011563 A1 * 1/2012 Newton ..... H04L 63/1425 726/1
2012/0192253 A1 * 7/2012 Betsch ..... G06F 21/31 726/4
2013/0029641 A1 * 1/2013 Hickie ..... G06F 21/604 455/411
2013/0304512 A1 * 11/2013 Seshadri ..... G06F 19/321 705/3
2013/0332484 A1 * 12/2013 Gajic ..... G06F 17/30286 707/770
2013/0346104 A1 12/2013 Pillai
2014/0108046 A1 * 4/2014 Echeverria Cabrera ..... G06F 21/6245 705/3
2014/0114826 A1 * 4/2014 Lopez ..... G06Q 30/04 705/34
2014/0189808 A1 * 7/2014 Mahaffey ..... H04L 63/083 726/4
2015/0100347 A1 * 4/2015 Nikam ..... G16H 10/60 705/3
2015/0127937 A1 * 5/2015 Ali ..... G06F 21/6218 713/165
2015/0169650 A1 * 6/2015 Gajic ..... G06F 17/30286 707/609
2015/0205973 A1 * 7/2015 Huh ..... G06F 21/6218 726/16
2015/0262194 A1 * 9/2015 Dunlop ..... G06Q 30/0185 705/318
2016/0036826 A1 * 2/2016 Pogorelik ..... H04L 63/105 726/1
2016/0042014 A1 * 2/2016 Jalan ..... H04L 67/1012 707/610
2016/0188898 A1 * 6/2016 Karinta ..... G06F 16/172 726/4
2016/0294548 A1 * 10/2016 Qian ..... H04L 63/062

OTHER PUBLICATIONS

First Examination Report dated Jan. 7, 2020 issued in connection with European Patent Application No. 16 184 681.1 (5 pages total).

* cited by examiner

600

| | Policies/ Capabilities | Master Admin. Module 208 | Information Module 202 | Organization Module 204 | Gatekeeper Module 206 |
|---|---|---|---|---|---|
| Delegation | A.1 Assign to Master Admin. Policy | X | | | |
| | A.2 Assign to Information Policy | X | | | |
| | A.3 Assign to Organization Policy | X | | | |
| | A.4 Assign to Gatekeeper Policy | | | X | |
| Query permissions | B.1 Explore meta-data | | X | X | X |
| | B.2 Query data for aggregated results | | X | X | X |
| | B.3 Query sensitive attributes/values | | X | X | X |
| | B.4 Set granularity limits or "rule of small numbers" | | X | X | X |
| | B.5 Set protocol based permissions | | X | | |
| Extract | C.1 Extract patient level data | | X | X | X |
| | C.2 Extract sensitive attributes/values | | X | X | X |
| | C.3 Set protocol based permissions | | X | | |
| Tools | D.1 Set access to tools | | | X | X |
| | D.2 Set allowed analytics | | | X | X |

FIG. 6

SYSTEM AND METHOD FOR PROVIDING MULTI-LAYERED ACCESS CONTROL

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*CROSS REFERENCE TO RELATED APPLICATIONS*

*This application is a reissue of U.S. Pat. No. 10,726,148, which issued on Jul. 28, 2020, entitled, "SYSTEM AND METHOD FOR PROVIDING MULTI-LAYERED ACCESS CONTROL", the contents of which is incorporated herein by reference in its entirety.*

BACKGROUND

Field of the Invention

Embodiments of the present invention generally relate to data security and access techniques, and, in particular, to a system and method for providing access to datasets.

Description of Related Art

Software applications and services generally use various mechanisms for authentication and/or authorization of a user to access data, such as healthcare data, from datasets. Privacy concerns are especially prominent for healthcare data. These privacy concerns can vary by country, data owner, commercial owner, or organization using the data. Typically, data owners limit a data user's activities contractually. For example, a dataset owner may limit a user's access to medical history of a patient stored in a dataset. However, these limitations do not provide assurance to the data owner that their datasets are used fully within the restrictions laid out contractually. Further, conventional techniques that do not allow privacy specific settings cannot be used to control access to healthcare data. However, the privacy specific settings lack privacy protection functionality required for commercial and/or scientific utilization of datasets. In addition, conventional techniques used for permitting users to access datasets takes time, effort and competence and therefore, data owners implement incomplete permission models, which in turn limit user searches. Further, the conventional techniques limit users to access healthcare data within a single country and therefore, do not allow users to access data on a geographically-dispersed or distributed datasets. The users can access the datasets within the country based on the predefined privacy specific settings. Further, the authentication and/or authorization are accomplished by using a password, a response to challenge questions, or other credentials that may be validated against a stored Access Control List (ACL). For example, the user may be required to provide login credentials such as username and/or password to access data stored in the datasets. However, the conventional techniques for providing privacy specific settings to access data from datasets lack specificity, user friendliness, are time-consuming, and do not provide sufficient access control to geographically-dispersed or distributed protected data.

Therefore, improved techniques are required for providing data security and data access control.

SUMMARY

Embodiments in accordance with the present disclosure provide a computer-implemented method for providing multi-layered access control for distributed healthcare datasets. The method comprising: defining an information policy for each of one or more distributed healthcare datasets, wherein the information policy comprises one or more information access permissions; defining an organization policy for each of the one or more distributed healthcare datasets, wherein the organization policy comprises one or more license permissions for one or more organizations accessing the one or more distributed healthcare datasets; defining a user account master policy for each of the one or more distributed healthcare datasets, wherein the user account master policy comprises one or more account permissions assigned to one or more users of the one or more organizations; and generating a master user policy for each of the one or more users based on at least one of the information policy, the organization policy, the user account master policy, or a combination thereof, wherein the master user policy comprises one or more access control permissions for providing each of the one or more users access to the one or more distributed healthcare datasets.

Embodiments in accordance with the present disclosure provide a system for providing multi-layered access control for distributed healthcare datasets. The system comprising: an information module configured to define an information policy for each of one or more distributed healthcare datasets, wherein the information policy comprises one or more information access permissions; an organization module configured to define an organization policy for each of the one or more distributed healthcare datasets, wherein the organization policy comprises one or more license permissions for one or more organizations accessing the one or more distributed healthcare datasets; a user account master module configured to define a user account master policy for each of the one or more distributed healthcare datasets, wherein the user account master policy comprises one or more account permissions assigned to one or more users of the one or more organizations; and a user access module configured to generate a master user policy for each of the one or more users based on at least one of the information policy, the organization policy, the user account master policy, or a combination thereof, wherein the master user policy comprises one or more access control permissions for providing each of the one or more users access to the one or more distributed healthcare datasets.

Embodiments in accordance with the present disclosure provide a computer-implemented method for providing multi-layered access control for distributed healthcare datasets. The method comprising: defining an information policy for each of one or more distributed healthcare datasets, wherein the information policy comprises one or more information access permissions; defining an organization policy for each of the one or more distributed healthcare datasets, wherein the organization policy comprises one or more license permissions for one or more organizations accessing the one or more distributed healthcare datasets; defining a user account master policy for each of the one or more distributed healthcare datasets, wherein the user account master policy comprises one or more account permissions assigned to one or more users of the one or more organizations; generating a master user policy for each of the one or more users based on at least one of the information policy, the organization policy, the user account master policy, or a combination thereof, wherein the master user policy comprises one or more access control permissions for providing each of the one or more users access to the one or more distributed healthcare datasets; and defining a master administrator policy, wherein the master administrator policy comprises one or more master permissions for control of at least one of the information policy, the organization policy, or a combination thereof.

The preceding is a simplified summary of embodiments of the disclosure to provide an understanding of some aspects of the disclosure. This summary is neither an extensive nor exhaustive overview of the disclosure and its various embodiments. It is intended neither to identify key or critical elements of the disclosure nor to delineate the scope of the disclosure but to present selected concepts of the disclosure in a simplified form as an introduction to the more detailed description presented below. As will be appreciated, other embodiments of the disclosure are possible utilizing, alone or in combination, one or more of the features set forth above or described in detail below.

BRIEF DESCRIPTION OF THE DRAWINGS

The above and still further features and advantages of the present invention will become apparent upon consideration of the following detailed description of embodiments thereof, especially when taken in conjunction with the accompanying drawings wherein like reference numerals in the various figures are utilized to designate like components, and wherein:

FIG. 6 is an exemplary table illustrating multi-layered policy permissions, according to an embodiment of the present disclosure;

Figure 1:
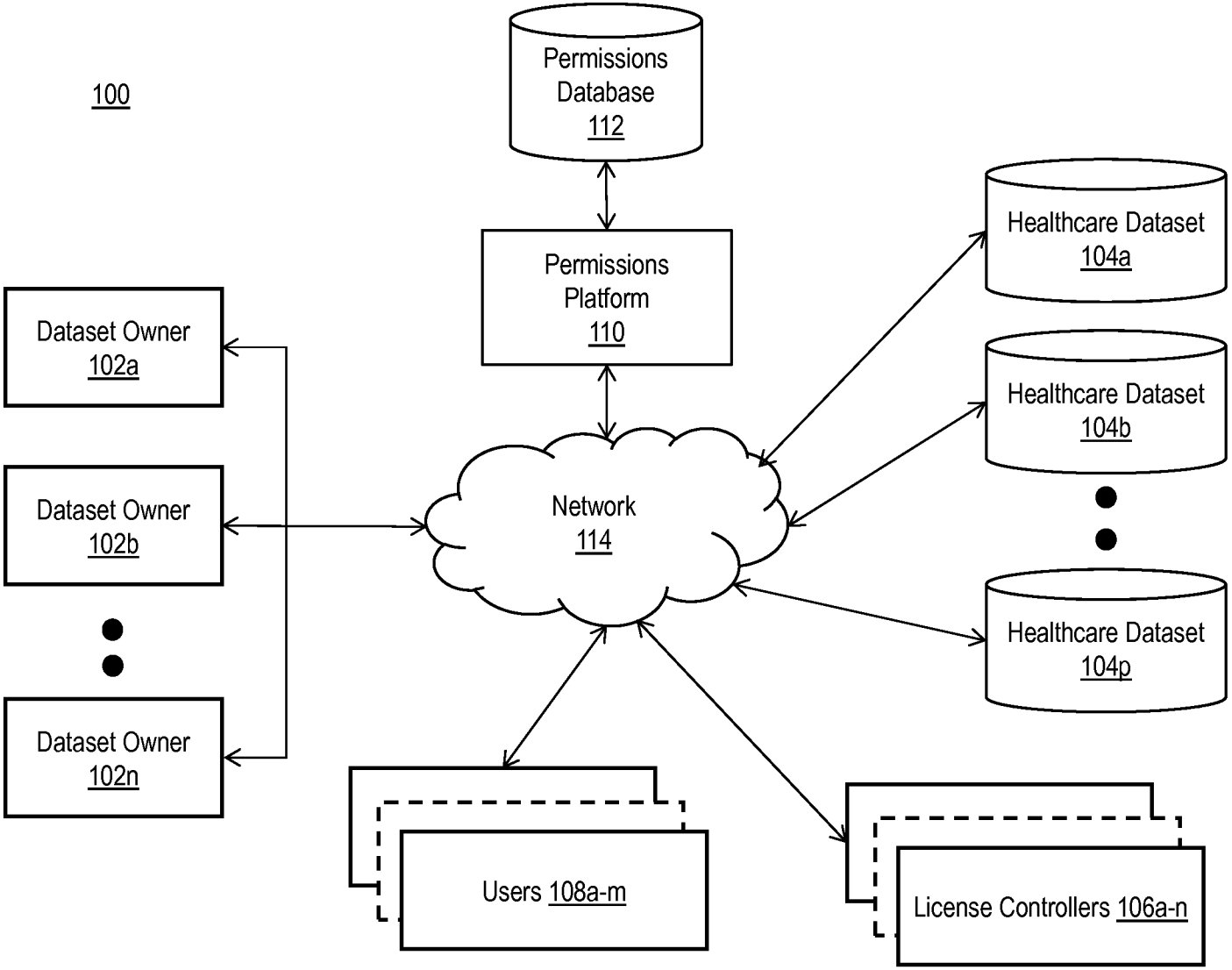
FIG. 1 depicts a system for providing multi-layered access control for distributed healthcare datasets, according to an embodiment of the present disclosure.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures. Optional portions of the figures may be illustrated using dashed or dotted lines, unless the context of usage indicates otherwise.

DETAILED DESCRIPTION

The disclosure will be illustrated below in conjunction with an exemplary digital information system. Although well suited for use with, e.g., a system using a server(s) and/or database(s), the disclosure is not limited to use with any particular type of system or configuration of system elements. Those skilled in the art will recognize that the disclosed techniques may be used in any system or process in which it is desirable to manage data and to provide it to clients based on their preferences.

The exemplary systems and methods of this disclosure will also be described in relation to software, modules, and associated hardware. However, to avoid unnecessarily obscuring the present disclosure, the following description omits well-known structures, components and devices that may be shown in block diagram form, are well known, or are otherwise summarized.

In the following detailed description, numerous specific details are set forth in order to provide a thorough understanding of embodiments or other examples described herein. In some instances, well-known methods, procedures, components and circuits have not been described in detail, so as to not obscure the following description. Further, the examples disclosed are for exemplary purposes only and other examples may be employed in lieu of, or in combination with, the examples disclosed. It should also be noted the examples presented herein should not be construed as limiting of the scope of embodiments of the present invention, as other equally effective examples are possible and likely.

As used herein, the term "module" refers generally to a logical sequence or association of steps, processes or components. For example, a software module may comprise a set of associated routines or subroutines within a computer program. Alternatively, a module may comprise a substantially self-contained hardware device. A module may also comprise a logical set of processes irrespective of any software or hardware implementation.

A module that performs a function also may be referred to as being configured to perform the function, e.g., a data module that receives data also may be described as being configured to receive data. Configuration to perform a function may include, for example: providing and executing computer code in a processor that performs the function; providing provisionable configuration parameters that control, limit, enable or disable capabilities of the module (e.g., setting a flag, setting permissions, setting threshold levels used at decision points, etc.); providing a physical connection, such as a jumper to select an option, or to enable/disable an option; attaching a physical communication link; enabling a wireless communication link; providing electrical circuitry that is designed to perform the function without use of a processor, such as by use of discrete components and/or non-CPU integrated circuits; energizing a circuit that performs the function (e.g., providing power to a transceiver circuit in order to receive data); and so forth.

The term "computer-readable medium" as used herein refers to any tangible storage and/or transmission medium that participate in storing and/or providing instructions to a processor for execution. Such a medium may take many forms, including but not limited to, non-volatile media, volatile media, and transmission media. Non-volatile media includes, for example, NVRAM, or magnetic or optical disks. Volatile media includes dynamic memory, such as main memory. Common forms of computer-readable media include, for example, a floppy disk, a flexible disk, a hard disk, a magnetic tape, or any other magnetic medium, magneto-optical medium, a CD-ROM, any other optical medium, punch cards, paper tape, any other physical medium with patterns of holes, RAM, PROM, EPROM, FLASH-EPROM, solid state medium like a memory card, any other memory chip or cartridge, a carrier wave as described hereinafter, or any other medium from which a computer can read. A digital file attachment to e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored.

FIG. 1 depicts a system 100 for providing multi-layered access control over distributed healthcare datasets, according to an embodiment of the present disclosure. As discussed above, privacy and security are important while providing data access and control. Access control is extremely critical for healthcare data. In an embodiment, the healthcare datasets 104a-p may include information regarding a patient or a healthcare specialist, for example, name, age, date of birth, occupation, home address, office address, medical history, medical reports, details of the concerned doctor, work experience of doctors, type of injury or disease, and the like. At least some of this sensitive patient health information data is protected by law (e.g., Healthcare Information Portability and Accountability Act ("HIPAA," codified at 42 U.S.C. § 300gg and 29 U.S.C § 1181 et seq. and 42 USC 1320d et seq.) in the U.S.) and must be treated in a way that maintains patient privacy. Such information is termed protected health information (PHI). Access to healthcare dataset 104 by an unauthorized entity may lead to violation of the privacy or security of the patients and specialists recorded in the datasets. In one embodiment, the information in the healthcare dataset 104 may be pseudo-anonymized. For example, the information such as the name, home address, or the social security number may be removed or anonymized. The system 100 provides access control over the healthcare datasets 104. In one embodiment, the system 100 enables enforcement of government or public healthcare regulations. Further, the system 100 enables provision of permission options for the healthcare dataset 104 that reflect existing privacy and potential future protection practices.

As shown, each dataset owner 102a-n may maintain and provide one or more healthcare datasets 104. Examples of the dataset owner 102 include, but not restricted to, a healthcare research organization, a pharmaceutical company, a data aggregator, and the like. In an embodiment, the dataset owners 102 and the healthcare datasets 104 may be distributed geographically and may be connected over a network 114. For example, the healthcare dataset 104a may be maintained in United States by the dataset owner 102a, while the healthcare dataset 104b may be maintained in Canada by the dataset owner 102b. A person skilled in the art will appreciate that various geographically distributed arrangements of the healthcare datasets 104 and the dataset owners 102 may be realized. The dataset owners 102 may desire to appropriately control the access of the datasets provided by them. For instance, access to a part of the healthcare dataset 104 maintained in Canada may be restricted to usage within Canada. Geographic locations for geographical boundary restrictions may be determined by, e.g., IP addresses. A permissions platform 110 of the system 100 enables access control over the healthcare datasets 104. In an embodiment, the permissions platform 110 may be maintained by an organization enabling consolidated access to geographically distributed healthcare datasets. Further, the access to the information in the healthcare datasets 104 may be controlled based on the subscriptions or licenses. For example, a research organization may license one or more healthcare datasets 104 such as diseases database to perform research on potential medicines or protocols.

In an embodiment, one or more users 108a-m access the healthcare datasets 104 through the permissions platform 110. Examples of the users 108 include, but are not restricted to, an organization, one or more users of the organization, independent researchers, and the like. In an exemplary scenario, the permissions platform 110 enables one or more users of a research organization to access the healthcare datasets 104. As shown, the users 108 may communicate with the permissions platform 110 over the network 114. For example, the network 114 may be a telephony network, a wireless network, a data network, a service provider data network, the Internet, and the like. For illustrative purposes, the network 114 may be any suitable wired, wireless, or combination thereof networks, which are managed by one or more service providers. For example, the telephony network may include, but is not restricted to, a circuit-switched network such as the Public Switched Telephone Network (PSTN), an Integrated Services Digital Network (ISDN), a Private Branch Exchange (PBX), a Session Initiation Protocol (SIP) based network, or other like networks.

In an embodiment, the permissions platform 110 defines multi-layered access control policies for controlling the access to the distributed healthcare datasets 104. Further, each policy may include one or more permissions defined for controlling the access to the healthcare datasets 104. In one embodiment, the permissions platform 110 may define an information policy for each of the distributed healthcare datasets 104. The information policy may include information access permissions to the healthcare datasets 104, as desired by the dataset owners 102. In an exemplary scenario, if the dataset owner 102 decides to deny access permission to an organization to a dataset, then the permissions platform 110 may define an appropriate information policy based on the information access permissions. In another exemplary scenario, the information policy defined by the permissions platform 110 may permit access to only a subset of the healthcare dataset 104. Therefore, the permissions platform 110 enables the dataset owners 102 to control access to the data owned or maintained by them.

In one embodiment, the permissions platform 110 may define an organization policy that may include one or more license permissions for an organization taking a license or subscription to healthcare datasets 104. In an exemplary scenario, the permissions platform 110 may enable license or subscription controllers 106a-n to define the license permissions for an organization to access the healthcare dataset 104a and healthcare dataset 104b, but not healthcare dataset 104c based on a license taken by the organization. Therefore, the access of the organization is restricted to datasets permitted in the organization policy. In an embodiment, the license controller 106 may be a service provider providing subscriptions or licenses to the users 108 for accessing the healthcare datasets 104 over the network 114.

In an embodiment, the organization policy may inherit the permissions from the information policy. Consequently, the access permission of the organization may be defined based on both the information access permissions and the license permissions. For example, the organization may be permitted access to only a part of the healthcare dataset 104a and the healthcare dataset 104b based on the permissions defined in the information policy.

In one embodiment, the permissions platform 110 may define a user account master policy, including one or more account permissions for one or more users of an organization to access the healthcare datasets 104. The account permissions may be required by an organization having license of the healthcare datasets 104 to control access by the users of the organization. In an exemplary scenario, the organization having license to the healthcare dataset 104a may desire to permit its users only a part of data from the healthcare dataset 104a or a part of the functionality of the permissions platform 110. For example, the account permissions may restrict the access of one or more analysis tools provided by the permissions platform 110 to the users 108.

In one embodiment, the permissions platform 110 may generate a master user policy for each of the users 108 based on the information policy, the organization policy, the user account master policy, or a combination thereof. In an embodiment, the information policy, the organization policy, and the user account master policy have a hierarchical architecture. Therefore, the permissions defined in the each of these policies are cascaded to generate a master user policy having one or more access control permissions. Consequently, the information access permissions defined in the information policy may be further restricted by the license permissions defined in the organization policy, and the license permissions may be further restricted by the account permissions of the user account master policy. Therefore, multi-layered hierarchical policy architecture is provided by the permissions platform 110. The policies and permissions are explained further in detail in conjunction with FIG. 2.

In one embodiment, the permissions platform 110 may define a master administrator policy. The master administrator policy may include master permissions for controlling the information policy, the organization policy, the user account master policy, or a combination thereof. In an embodiment, the master permissions may define the roles and access of one more administrators of the permissions platform 110. The administrator may be for example, an individual or an entity enabled to define one or more permissions for a policy. For example, the master administrator policy may enable one or more administrators to decide permissions over healthcare datasets 104.

In one embodiment, the permissions platform 110 stores the information policy, the organization policy, the user account master policy, the master user policy, the master administrator policy, and the associated permissions in a permissions database 112. The permissions database 112 may be communicatively coupled to the permissions platform 110 locally, in one embodiment. In another embodiment, the permissions database 112 may be accessible over the network 114. For example, the permissions database 112 may be distributed across the network 114. In one embodiment, the permissions database 112 may further include information such as user credentials, dataset owner credentials, licensee organization credentials, or any other information required by the permissions platform 110 to function.

As noted previously, the permissions platform 110 enables the users 108 to access the healthcare datasets 104. By way of example, the permissions platform 110 receives one or more queries from the user 108 for accessing the healthcare dataset 104. Subsequently, the permissions platform 110 determines one or more access control permissions for the user 108 based on the defined master user policy. Thereafter, the permissions platform 110 provides, to the user 108, access to the data based on the one or more access control permissions. In an embodiment, at least a part of the data is made accessible to the user 108 based on the master user policy. In another embodiment, the user 108 is blocked from querying the dataset based on the access control permissions defined in the master user policy.

In one embodiment, the permissions platform 110 may provide a web based user interface. For example, a Hyper Text Markup Language (HTML) based user interface may be provided that may be accessed over communication protocols such as, but not limited to, Hyper Text Transfer Protocol (HTTP). Therefore, the users 108 may communicate with the permissions platform 110 over a computer network or the Internet.

Figure 2:
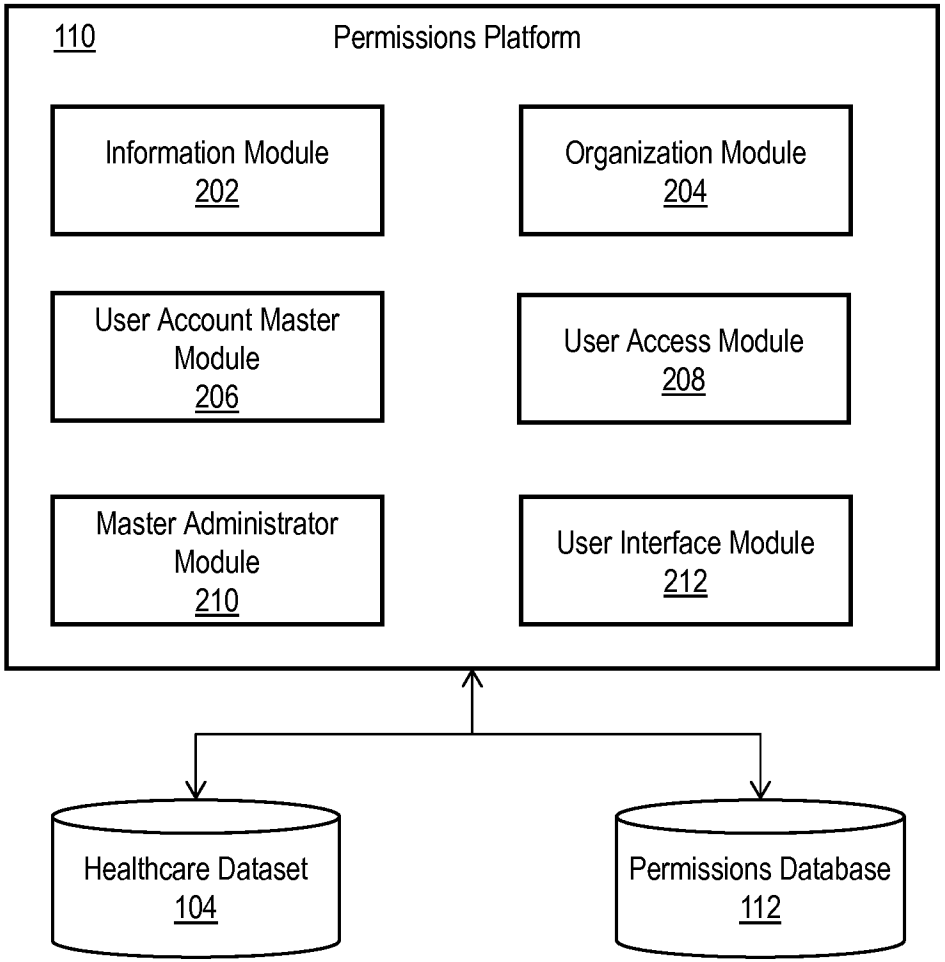
FIG. 2 depicts components of a permissions platform, according to an embodiment of the present disclosure.

FIG. 2 is a diagram of components of the permissions platform 110, according to an embodiment of the present disclosure. The permissions platform 110 may include various executable modules for performing one or more computing, data processing, or network based instructions that in combination for providing multi-layered access control for distributed healthcare datasets 104. Such modules may be implemented in hardware, firmware, software, or a combination thereof. As shown, the permissions platform 110 may include an information module 202, an organization module 204, a user account master module 206, a user access module 208, a master administrator module 210a, and a user interface module 212 according to an embodiment of the present invention.

In one embodiment, the information module 202 may define the information policy including the information access permissions for the healthcare datasets 104. In an embodiment, the information module 202 may receive the information access permissions from the dataset owners 102. In another embodiment, the information access permissions may be defined by an administrator of the information access policy by using the information module 202. The information access permissions may include one or more query permissions, and one or more data extract permissions. The query permissions may refer to permissions for querying the healthcare datasets 104. In one embodiment, the query permissions may further include, but not restricted to, a permission for exploring meta-data of healthcare dataset 104, a permission for querying data for aggregated results, a permission for querying sensitive attributes, a permission for setting granularity limits, a permission for setting protocol-based permissions. The permission for exploring the metadata enables or withholds a user or an organization from accessing information about the overall dataset. For example, the metadata may refer to the type of information contained in the healthcare dataset 104, such as high level information about the patient population by gender distribution, age distribution, and the like. In one embodiment, the meta-data of a healthcare dataset 104 may include only high-level aggregated information, therefore permission for exploring the meta-data may be granted for all healthcare datasets 104.

The permission for querying data for aggregated results defines whether a user or an organization may access subsets or cuts of healthcare datasets 104. Further, the querying permission may restrict the user to query only a proportion of the healthcare datasets 104. Moreover, the proportion of healthcare datasets 104 selected for query may be randomized to further control the access. In one embodiment, aggregated results may include only high-level or subset of information, therefore permission for querying data for aggregated results may be granted for all healthcare datasets 104.

The healthcare datasets 104 may include one or more sensitive attributes and values that may affect the privacy of data. The information from sensitive attributes may enable identification of a patient. For example, the attributes may include, but are not restricted to, a patient identification (ID), medical history, genetic attributes, a link ID, a physician ID, a plan ID, a site ID, a ward number in a hospital, geo-codes, a specific level of the geo-code access (e.g., access to ZIP, and level of digits accessible in ZIP), and the like. Examples of values associated with the attributes may include, but not restricted to, Human Immunodeficiency Virus (HIV), Sexually Transmitted Diseases (STDs), psychological conditions, age below 18 years, and the like. Access to sensitive attributes and values may be defined by the permission for querying sensitive attributes. Therefore, a user may be able to query the healthcare dataset 104 based on the attributes and values allowed by the permissions. Consequently, the risk of privacy breach or identification of patients from the datasets is reduced.

Typically, an aggregated set of results is generated based on queries to datasets. The aggregated results may be a threat to privacy when the number of results is very low. For example, identification of patient from a total of seven results is easier than a total of 100 results. The permission for setting granularity limits defines the limit on the number of results below which the results of the query may not be presented to a user. By way of example, the results of query may not be displayed when the number of results is below a range of 6 to 10 patients. The permission may be referred to as "the rule of small numbers".

The permission for setting protocol-based permissions enable restrictive access to the queries and on the users performing protocol-based research. Generally, protocol-based research is a common highly restrictive framework for accessing healthcare datasets 104. Further, the protocol-based permissions may enable access to analytical tools or reports to the users performing the protocol-based research. In an exemplary scenario, access to datasets and reports may be defined for a principal investigator of a protocol-based research by setting protocol-based permissions. Therefore, dataset owners 102 may have direct control of users of the healthcare datasets 104.

The data extract permissions of the information policy include permissions for users 108 to extract data from the healthcare datasets 104. In one embodiment, the data extract permissions may further include, but not restricted to, permission for extracting patient level data, permission for extracting sensitive attributes, and a permission to set protocol-based permissions. The permission for extracting patient level data controls the amount and level of patient data that may be extracted or exported from the healthcare dataset 104. For example, the data extract may be restricted by an overall limit to the number of extractions performed, a percentage of dataset extracted or a number of records extracted. In one embodiment, key usage limits may be displayed before extraction of the data. The permission for extracting sensitive attributes enable or withholds a user or an organization from extracting the sensitive attributes. The protocol-based permissions defines data extract access of a user for a protocol-based research. In one embodiment, different information policies may be defined for different users or organizations. Therefore, the information module 202 enables dataset owners 102 to provide detailed and granular access control permissions for healthcare dataset 104.

In one embodiment, the organization module 204 may define the organization policy including the license permissions for the healthcare datasets 104. In an embodiment, the organization module 204 may receive the license permissions from the license controller 106. As discussed above, the license controller 106 may be a service provider providing subscriptions or licenses to users for accessing the healthcare datasets 104. In one embodiment, the organization policy maintains or restricts the permissions defined in the information policy. The organization policy may include delegation permissions, one or more query permissions, one or more extract permissions, and one or more tool permissions.

In one embodiment, the delegation permissions enable nomination of a user account master such as a user account master at an organization for controlling access to the healthcare dataset 104. The user account master may be an individual that may define the user accounts for accessing the datasets. The query permissions of the organization policy may further restrict the permissions defined in the information policy for querying the healthcare dataset 104. For example, a dataset that is not licensed by the user may not be allowed to be queried, even when there are no restrictions defined for the user in the information policy. The query permissions of the organization policy may further enable setting of the access period for the healthcare dataset 104 based on the subscription or license. For example, the license may be set to auto termination based on the organization policy. Furthermore, the query permissions of the organization policy may define refresh periods of the healthcare dataset 104 licensed by the organization. For example, the refresh period may be set to weekly or monthly based on the license or subscription terms and conditions.

The extract permissions of the organization policy may further restrict the permissions defined in the information policy for extracting information from the healthcare dataset 104. In one embodiment, the extract permissions of the organization policy may define the limits on extraction of a number of results for an organization. By way of example, the information policy may define a dataset that can be accessed by the organization, and then the organization policy further restricts extraction of only the first one thousand results. Therefore, the network capacity and bandwidth within the organization may be controlled by the permissions. The license controller 106 may provide the organization with access to tools associated with analysis of the healthcare dataset 104. The tools permissions of the organization policy define the access to one or more tools and the number of users for the tools. Further, the tools permissions may define the usage limits to the tools in the organization.

In one embodiment, the user account master module 206 may define the user account master policy including the account permissions for the healthcare datasets 104. In an embodiment, the user account master module 206 may receive the account permissions from a user account master of the organization. As discussed above, the user account master may be an administrator of user accounts in the organization. In one embodiment, the user account master policy maintains or restricts the permissions defined in the organization policy. In one embodiment, the user account master policy distributes permissions defined in the organization policy to the users of the organization. In an exemplary scenario, the user account master policy may enable account permissions for a maximum of five users in an organization if the license or subscription is taken for five licenses. In one embodiment, the user account master module 206 may generate and display an error if additional users apart from the licensed number attempt to access to the healthcare dataset 104. In one embodiment, the account permissions may define different level of access to different users in the organization.

In one embodiment, the user access module 208 may generate a master user policy for each of the users 108 based on the information policy, the organization policy, the user account master policy, or a combination thereof. The master user policy may include access control permissions for providing each of the users 108 access to the distributed healthcare datasets 104. In one embodiment, the access control permissions of the master user policy may inherit the permissions defined in the information policy, the organization policy, and the user account master policy. As noted previously, the user account master policy inherits the permissions of the organization policy, which in turn inherits the permissions defined in the information policy. Therefore, the access control permissions provide enhanced security and full privacy control of the healthcare dataset 104.

In one embodiment, the master administrator module 210 may define a master administrator policy. The master administrator policy may include the master permissions to control the information policy, the organization policy, the user account master policy, or a combination thereof. In one embodiment, the master permissions may include permissions for delegating administrator roles to one or more individuals. For example, an administrator delegated for the organization policy may set or manage the permissions defined in the organization policy. In one embodiment, the master administrator policy may be the same for all geographically distributed healthcare dataset 104. As noted previously, the information policy, the organization policy, the user account master policy, the master user policy, or the master administrator policy, or a combination thereof, are stored in the permissions database 112.

In one embodiment, the user interface module 212 may receive one or more queries from the user 108 and provide data from the healthcare dataset 104, according to one embodiment. The user interface module 212 may check for the master user policy associated with the user 108 from the user access module 208. Subsequently, the results of the queries are presented to the users 108. In one embodiment, the user interface module 212 may provide a web based Graphical User Interface (GUI). For example, a Hyper Text Markup Language (HTML) based user interface may be provided that may be accessed over communication protocols such as, but not limited to, Hyper Text Transfer Protocol (HTTP). In one embodiment, the user interface provided by the user interface module 212 may be used for setting the permissions and the policies by the dataset owners 102, license controllers, user account masters, or other administrators of the permissions platform 110.

Figure 3:
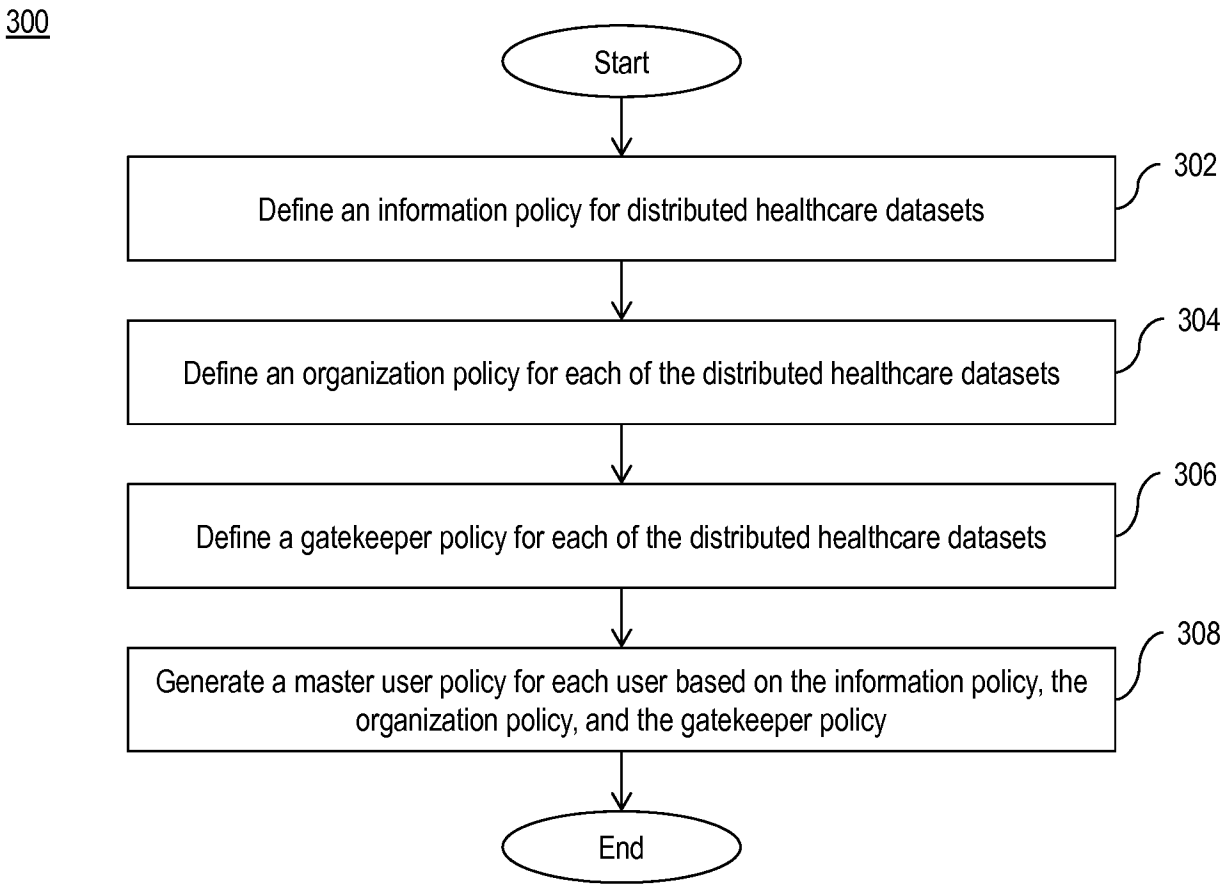
FIG. 3 illustrates a flowchart of a method for providing multi-layered access control for distributed healthcare datasets, according to an embodiment of the present disclosure.

FIG. 3 illustrates a flowchart of a process 300 for providing multi-layered access control for distributed healthcare datasets, according to an embodiment of the present disclosure. The process 300 begins at step 302, at which an information policy is defined for the healthcare dataset 104. Further, the information policy may include one or more information access permissions. In one embodiment, the information access permissions for the information policy may be received by the dataset owner 102 associated with the distributed healthcare datasets 104. As noted previously, the dataset owner 102 may provide the information access permissions by using the permissions platform 110.

Next, the control of the process 300 proceeds to step 304, at which an organization policy is defined for each of the distributed healthcare dataset 104. Further, the organization policy may include one or more license permissions. In one embodiment, the organization policy may be received from the license controller 106 or a third-party service provider that manages subscriptions or licenses to healthcare datasets 104. The third-party service provider may define organization policies for organizations to restrict the users to access sensitive healthcare data stored in the distributed healthcare dataset 104. As noted previously, the organization policy further restricts the permissions defined in the information policy.

Thereafter, the control of the process 300 proceeds to step 306, at which a user account master policy is defined for each of the distributed healthcare datasets 104. The user account master policy may include one or more account permissions that are assigned to one or more users of one or more organizations. As noted previously, the permissions of user account master policy may be provided by a user account master of the organization. Further, the user account master policy further restricts the permissions defined in the organization policy.

Next, the control of the process 300 proceeds to step 308, at which a master user policy is generated for each user based on the defined information policy, the organization policy, the user account master policy, or a combination thereof. The master user policy includes one or more access control permissions for providing each of the one or more users access to the one or more distributed healthcare datasets 104. In one embodiment, a master administrator policy is defined that includes one or more master permissions for control of at least one of the information policy, the organization policy, or a combination thereof.

Figure 4:
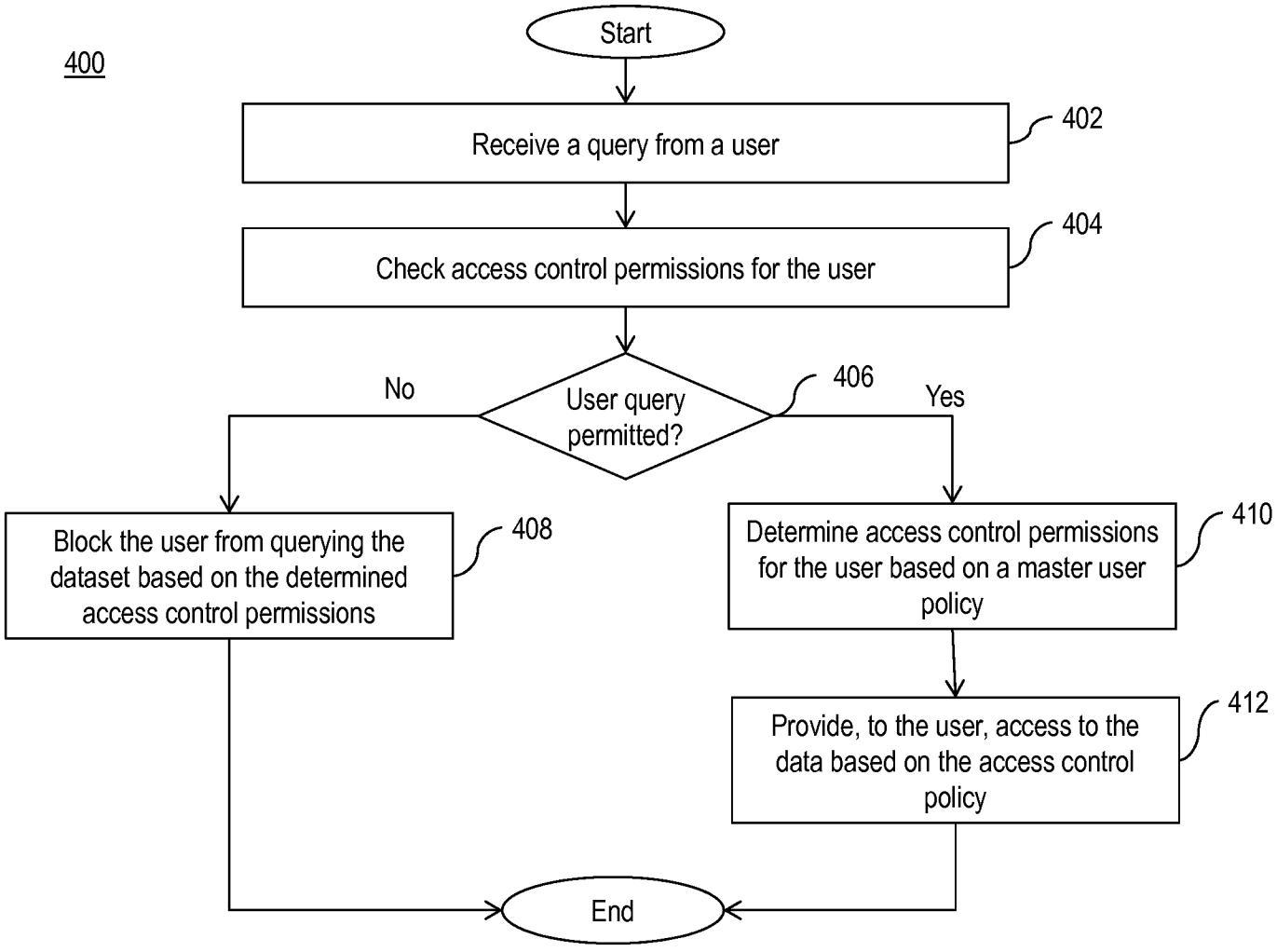
FIG. 4 illustrates a flowchart of a method for providing multi-layered access control for distributed healthcare datasets to a user, according to another embodiment of the present disclosure.

FIG. 4 illustrates a flowchart of a process 400 for providing multi-layered access control for distributed healthcare datasets, according to another embodiment of the present disclosure. The control of the process 400 proceeds to step 402, at which a user query is received. In one embodiment, the query may be received at the permissions platform 110 over the network 114 for accessing the distributed healthcare datasets 104. The query may be web based query or a local query in query formats such as, but not limited to, a Structured Query Language (SQL).

Control of process 400 proceeds to step 404, at which access control permissions for the user are checked. In one embodiment, the access control permissions may be checked based on the master user policy. As discussed above, the master user policy may be generated based on the information policy, the organization policy, the user account master policy, or a combination thereof. If the user is permitted to query, process 400 proceeds to step 406, at which it is determined whether the user is permitted to query the distributed healthcare dataset 104, and if allowed then the query would be executed on the distributed healthcare dataset 104. Otherwise, the user is restricted from querying the distributed healthcare dataset 104, and process 400 proceeds to step 408. In one embodiment, the query may be executed only on a portion of the healthcare dataset 104, based on the master user policy.

At step 408, the user is blocked from querying the distributed healthcare dataset 104 based on the one or more access control permissions, and process 400 ends.

At step 410, one or more access control permissions for the user are determined based on the master user policy. As noted previously, the access control permissions may include permissions to level of data access, one or more countries from which the data may be accessed, a time period in which data may be accessed, the amount of data (e.g., by "rule of small numbers"), and the like. Thereafter, control of process 400 proceeds to step 412, at which an access to the healthcare dataset 104 is provided to the user. In one embodiment, the data resulting from the query is not provided to the user based on the access control permissions. In an exemplary scenario, if the 'rule of small numbers' for results is set to three, and the number of results obtained from the query is three or fewer, then the results or data may not be displayed to the user.

Figure 5:
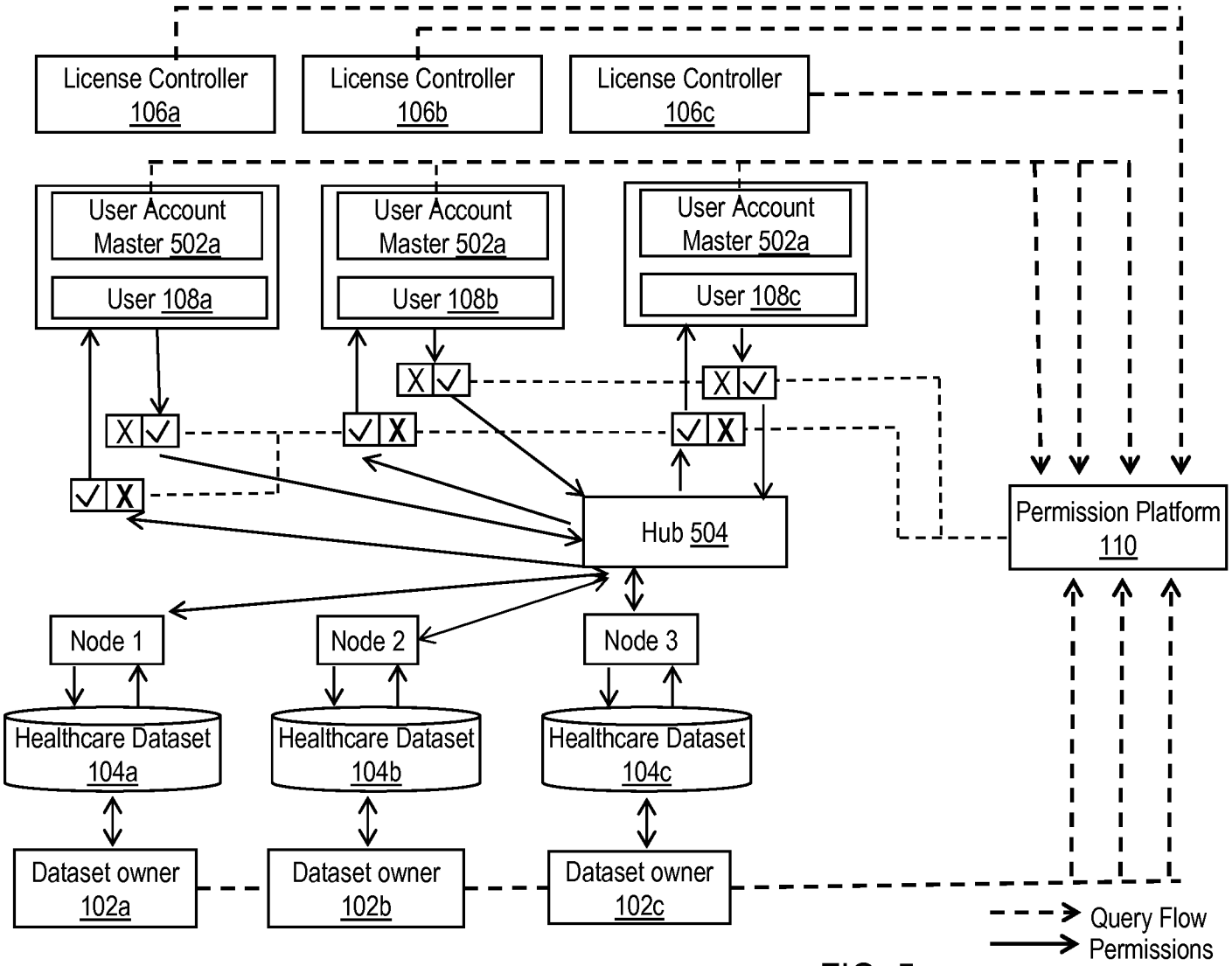
FIG. 5 illustrates an exemplary scenario for providing multi-layered access control for distributed healthcare datasets, according to an embodiment of the present disclosure.

FIG. 5 depicts an exemplary scenario for providing multi-layered access control for distributed healthcare datasets, according to an embodiment of the present disclosure. As shown, dataset owners 102a-c may be located in three different countries (for e.g., Canada, Britain, and Sweden). Further, the data associated with the dataset owners 102a-c is stored in distributed datasets such as a healthcare dataset 104a-c.

The healthcare dataset 104a-c may be for example, electronic medical records, a medical claims database, a pharmacology database, or the like. The dataset owners 102a-c provide permissions to the permissions platform 110 that further define information policies for the users 108a-c located in different geographic locations. Similarly, license controllers 106a-c provide permissions to the permissions platform 110 to define organization policies, and user account masters 502a-c provide permissions to the permissions platform 110 to define user account master policies that permit the users 108a-c to access data from the distributed healthcare datasets 104a-c. Further, the permissions platform 110 generates a master user policy by using the information policies, the organization policies, the user account master policies, or a combination thereof. As shown, the healthcare datasets 104a-c are geographically distributed and may be connected to separate network nodes Node 1, Node 2, and Node 3. Each of the nodes Node 1, Node 2, and Node 3 may then be connected to a hub 504. In one embodiment, the Nodes 1-3 may be data servers connecting the healthcare dataset 104a-c to the hub 504. Further, the hub 504 may be a data center comprising the information of the healthcare dataset 104a-c. In one embodiment, the hub 504 may provide a web based user interface for defining the permissions and accessing the data from the healthcare datasets 104.

The users 108a-c transmit queries to the permissions platform 110 to access data from the healthcare datasets 104a-c. Thereafter, the permissions platform 110 determines master user policies for the users 108a-c from the permissions database 112. The determined master user policy is provided to the hub 504 from where the users 108a-c may access data the healthcare datasets 104a.

FIG. 6 is an exemplary table 600 illustrating the cascading of multi-layered policy permissions, according to an embodiment of the present disclosure. As noted previously, the information policy, the organization policy, the user account master policy, and the master administrator policy have a hierarchical architecture. In one embodiment, the master administrator policy defined by the master administrator module 210 is at the highest level of hierarchy, followed by information policy defined by the information module 202, the organization policy defined by the organization module 204, and the user account master policy defined by the user account master module 206 in that order. Therefore, the permissions of the information policy are further restricted by the permissions of the organization policy, which are in turn further restricted by the permissions of the user account master policy.

As shown and also discussed above, the delegation permissions for the master administrator policy, the organization policy, and the information policy are defined and controlled by the master administrator module 210. The delegation permissions for the user account master policy may be defined by the organization module 204. Further, each of the information module 202, the organization module 204, and the user account master module 206 may define the query permissions for exploring meta-data, querying data for aggregated results, querying sensitive attributes and/or values, and set granularity limits. The information module 202 may further define permissions for setting protocol-based permissions. Furthermore, each of the information module 202, the organization module 204, and the user account master module 206 may define the extract permissions for extracting patient level data and extracting sensitive attributes and/or values. The information module 202 may further define extract permissions for setting protocol-based permissions.

The organization module 204 and the user account master module 206 may further define permissions for setting access to analytical tools, and set allowed access levels in the tools. For example, permissions both for accessing the tools and the allowed level of access may be defined.

Figure 7:
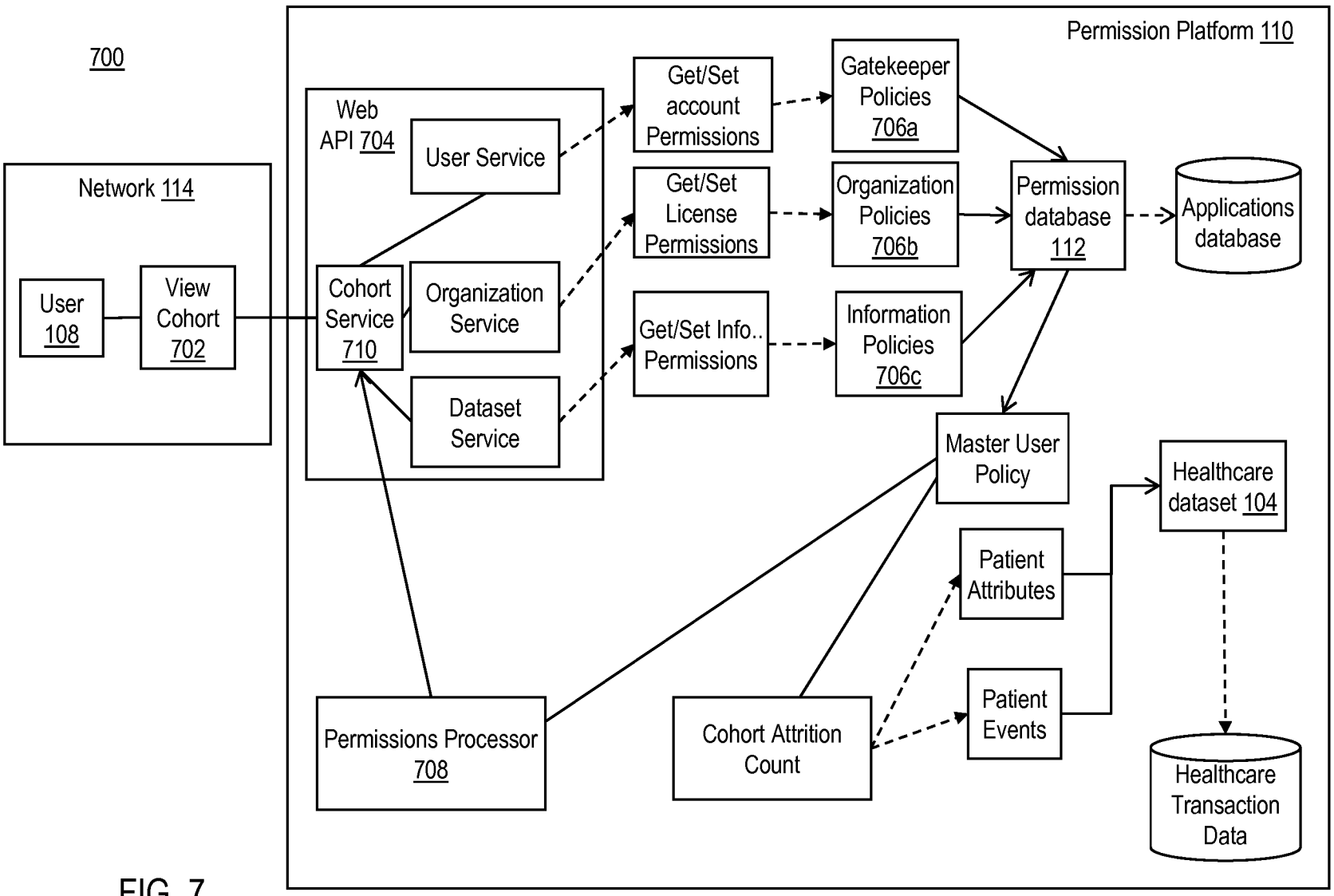
FIG. 7 depicts an exemplary block diagram of information flow in the permissions platform, according to an embodiment of the present disclosure.

FIG. 7 depicts an exemplary block diagram of information flow in the permissions platform 110, according to an embodiment of the present disclosure. The user 108 may use a web browser to request permission to view cohort 702 from a website hosted either on the Internet or on a local/on premise network, such as the communication network 114. The word "cohort" is used in epidemiology to define a set of people followed over a period of time. In particular, "cohort" refers to a group of people with defined characteristics who are followed up to determine incidence of, or mortality from, some specific disease, all causes of death, or some other outcome. In an exemplary scenario, the user may provide the permissions for accessing the healthcare datasets 104. In this case, the user may be a dataset owner, a license controller, a user account master or any other administrator authorized to set the permissions for the data access and control.

In one embodiment, the view of cohort 702 may be by use of a Hyper Text Markup Language (HTML) user interface that communicates with a web Application Program Interface (API) 704. Thereafter, a cohort function or service of the web API 704 may be executed. The cohort function or service may further execute services, such as a user service to get and/or set the account permissions defined by the user account master policies 706a, an organization service to get and/or set the license permissions for the organization policies 706b, and dataset service to get and/or set the information permissions for the information policies 706c. Subsequently, the policies 706a-c may be received or sent to the permissions database 112.

The permissions database 112 may use an applications database to generate a master user policy that is provided to the cohort service 710 via a permissions processor 708. In one embodiment, the permissions processor 708 provides a single complete master user policy in a JavaScript Object Notation (JSON) format. The cohort service 710 may then use the master user policy to provide access to the healthcare dataset 104. For example, when a cohort attrition count query is executed the master user policy is applied before providing the results. As shown, the patient attributes and patient events are queried from the healthcare dataset 104 to present healthcare transaction data. Therefore, the user querying the healthcare dataset 104 may be presented with the results in the form of healthcare transaction data after applying the permissions defined in the master user policy.

Figure 8:
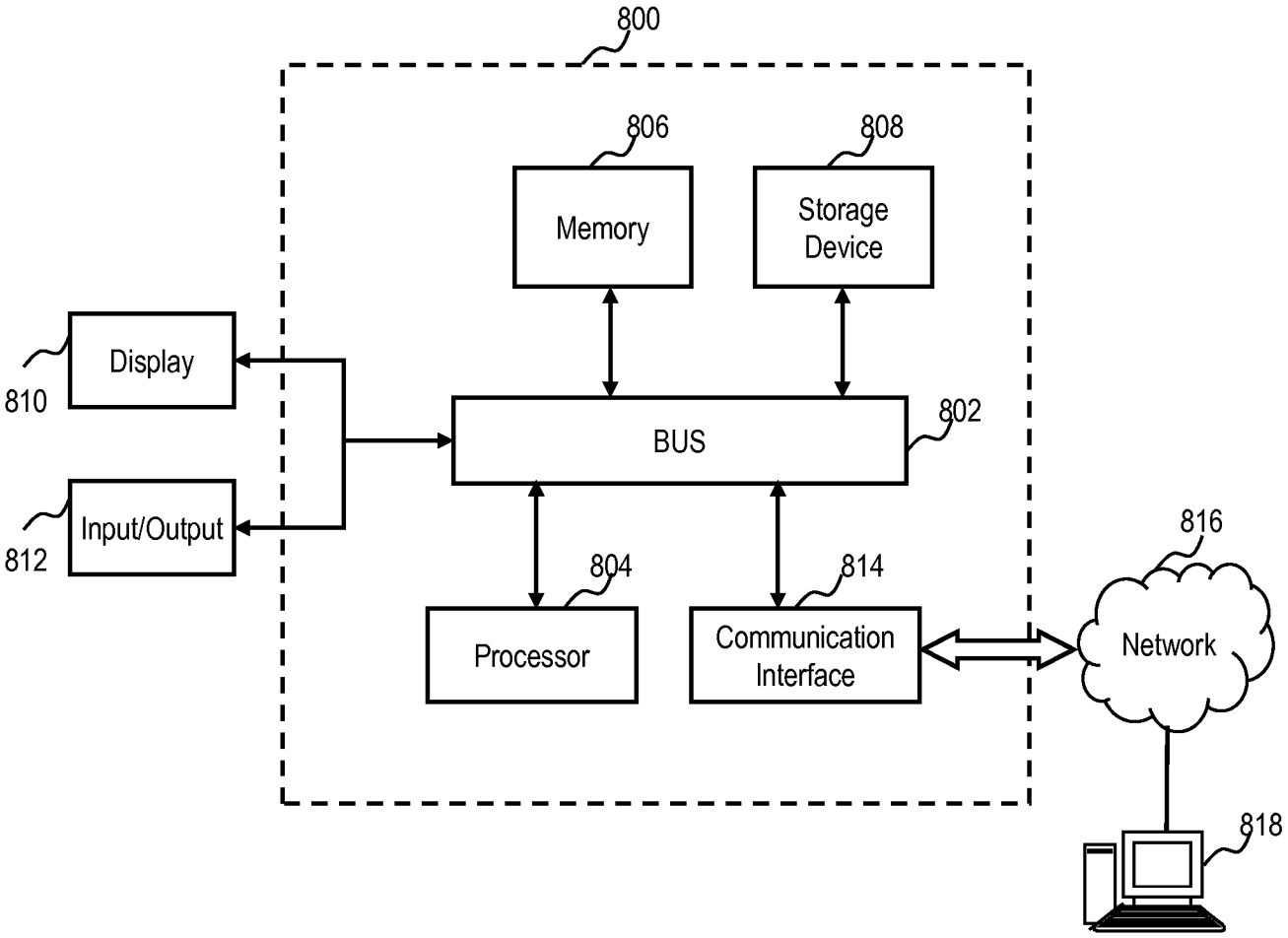
FIG. 8 depicts a computer system that can be used to implement various exemplary embodiments of the present disclosure.

FIG. 8 illustrates a computing system (e.g., a client) 800 on which exemplary embodiments may be implemented to provide multi-layered access control for distributed healthcare datasets. In one embodiment, the computing system 800 may be the permissions platform 110 that performs various functions to define and/or generate policies, such as an information policy, an organization policy, a user account master policy, and the like. The computing system 800 includes a bus 802 for communicating information and a processor 804 coupled to the bus 802 for processing information. The computing system 800 also includes a memory 806 connected to the bus 802 for storing the information and instructions to be executed by processor 804. Examples of the memory 806 may include a Random Access Memory (RAM), a Read Only Memory (ROM), or other static or dynamic storage for storing information and instructions for the processor 804. Further, the computing system 800 may include a storage device 808, such as a magnetic disk, a solid-state disk, or an optical disk, coupled to the bus 802 for storing information.

The computing system 800 may be coupled via the bus 802 to a display 810, such as a Cathode Ray Tube (CRT), a liquid crystal display, Light Emitting Diode (LED) flat panel display, etc. In an embodiment, the computing system 800 includes an input/output device 812, such as a keyboard, a mouse, or other pointing device for providing inputs or instructions.

The computing system 800 may also include a communication interface 814 coupled to the bus 802. The communication interface 814 provides connection of a remote computer 818 over a network 816, such as the communication network 114. Examples of communication interface 814 may include an Ethernet adapter, a Wi-Fi transceiver using an IEEE 802.11 protocol, and so forth. Examples of the network 816 may include, Local Area Network (LAN), Wide Area Network (WAN), or other wired or wireless networks. In an embodiment, the network 816 may be a cloud network that is a collection of hardware and software that form a shared pool of computing resources (e.g., networks, servers, storage, applications, services, etc.) that can be suitably provisioned to provide on-demand self-service, network access, resource pooling, and the like.

The disclosed methods may be readily implemented in software, such as by using object or object-oriented software development environments that provide portable source code that can be used on a variety of computer or workstation platforms. Alternatively, the disclosed system may be implemented partially or fully in hardware, such as by using standard logic circuits or VLSI design. Whether software or hardware may be used to implement the systems in accordance with various embodiments of the present invention may be dependent on various considerations, such as the speed or efficiency requirements of the system, the particular function, and the particular software or hardware systems being utilized.

While the foregoing is directed to embodiments of the present invention, other and further embodiments of the present invention may be devised without departing from the basic scope thereof. It is understood that various embodiments described herein may be utilized in combination with any other embodiment described, without departing from the scope contained herein. Further, the foregoing description is not intended to be exhaustive or to limit embodiments of the invention to the precise form disclosed. Modifications and variations are possible in light of the above teachings or may be acquired from practice of embodiments of the invention. Certain exemplary embodiments may be identified by use of an open-ended list that includes wording to indicate that the list items are representative of the embodiments and that the list is not intended to represent a closed list exclusive of further embodiments. Such wording may include "e.g.", "etc.," "such as," "for example", "and so forth", "and the like", etc., and other wording as will be apparent from the surrounding context.

No element, act, or instruction used in the description of the present application should be construed as critical or essential to embodiments of the invention unless explicitly described as such. Also, as used herein, the article "a" is intended to include one or more items. Where only one item is intended, the term "one" or similar language is used. Further, the terms "any of" followed by a listing of a plurality of items and/or a plurality of categories of items, as used herein, are intended to include "any of," "any combination of," "any multiple of," and/or "any combination of multiples of" the items and/or the categories of items, individually or in conjunction with other items and/or other categories of items.

Moreover, the claims should not be read as limited to the described order or elements unless stated to that effect. In addition, use of the term "means" in any claim is intended to invoke 35 U.S.C. § 112(f), and any claim without the word "means" is not so intended.

What is claimed is:

1. A *computer-implemented* method to provide permissions for users from different organizations to access health information of cohort members while assuring privacy and security of the cohort members' health information deposited in a plurality of datasets having different commercial owners who control the access to the datasets they own, [wherein the access is achieved via computing devices having a hardware processor communicatively connected to the plurality of datasets via a network,] the method comprising the steps of:

defining, [by the processor,]

an information policy including permissions set by the different commercial owners of each of the plurality of datasets for access to [the health information and granularity of the health information in] each of the plurality of the datasets,

[an organization policy including permissions derived from a plurality of licenses subscribed to by the respective organizations for accessing each of the plurality of datasets, and a user policy including account permissions selectively assigned to the users from each of the different organizations;]

generating a master policy [having access control permissions for access to each of the plurality of datasets for each of the users from each of the different organizations, wherein the master policy comprises] *for one or more users of an organization based on* the information policy, *an* organization policy, and [the] *a* user policy; and

[in response to a request from the computing device of the users:]

controlling[, by the processor,] access to [the] health information of [the] cohort members in the plurality of datasets based on the [access control permissions of the] master policy.

2. The method of claim 1, further comprising [a step of]: defining[, by the processor,] an administrator policy [including permissions] to control *at least one of* the information policy, *the user policy,* and the organization policy.

3. The method of claim [2] *1*, wherein [the administrator policy, the information policy,] *access permissions defined in the information policy are restricted by a license and/or subscription defined in* the organization policy[, and the user policy have a hierarchical architecture].

4. The method of claim [3] *1*, wherein [each of the plurality of licenses is restricted by] the information policy[, and the user policy is restricted by the information policy and the license] *permits access to a subset of the datasets.*

5. The method of claim 1, further comprising [a step of]: [blocking, by the processor, the users from querying, via their respective computing device, the plurality of datasets based on the generated access control permissions] *defining one or more license permissions for the organization to access the plurality of datasets.*

6. The method of claim 1, wherein the *organization policy inherits permission to access one or more of the datasets from the* information policy [further comprises at least one of a permission to explore meta-data, a permission to query data for aggregated results, a permission to query sensitive attributes, a permission to set protocol-based permissions, a permission to extract patient level data, and a permission to extract sensitive attributes].

7. The method of claim 1, [wherein each of the plurality of licenses comprises at least one of a permission to set a user account, a permission to set access restrictions, a permission to set access period, a permission to define refresh periods, a permission to define user limits, and a permission to define access tools] *further comprising:*

*permitting only a subset of the datasets to be accessed based on the master policy.*

8. A [system] *computer program product* to provide permissions for users from different organizations to access health information of cohort members while assuring privacy and security of the cohort members' health information deposited in a plurality of datasets having different commercial owners who control the access to the datasets they own, [wherein the access is achieved via computing devices having a hardware processor communicatively connected to the plurality of datasets via a network, the system comprising] *the computer program product comprising a tangible storage medium encoded with processor-readable instructions that, when executed by one or more processors, enable the computer program product to*:

[the processor configured to:]

define an information policy including permissions set by the different commercial owners of each of the plurality of datasets for access to [the health information and granularity limits of the health information in] each of the plurality of the datasets,

[an organization policy including permissions derived from a plurality of licenses subscribed to by the respective organizations for accessing each of the plurality of datasets, and a user policy including account permissions selectively assigned to the users from each of the different organizations;]

generate a master policy [having access control permissions for access to each of the plurality of datasets for each of the users from each of the different organizations, wherein the master policy comprises] *for one or more users of an organization based on* the information policy, *an* organization policy, and [the] *a* user policy; and

[in response to a request from the computing device of the users:]

control access to [the] health information of [the] cohort members in the plurality of datasets based on the [access control permissions of the master policy of the] master policy.

9. The [system] *computer program product* of claim 8, wherein the [processor is further configured to define an administrator policy including permissions to control the information policy, and the organization policy] *information policy includes one or more access permissions for one or more of the plurality of datasets.*

10. The [system] *computer program product* of claim [9] *8*, wherein the [administrator policy,] the information policy[, the organization policy, and the user policy have a hierarchical architecture] *permits access to only a subset of the datasets.*

11. The [system] *computer program product* of claim [10] *8*, wherein [each of the plurality of licenses is restricted by the information policy, and the user policy is restricted by the information policy and the license] *license controllers define one or more license permissions for the organization to access one or more of the datasets.*

12. The [system] *computer program product* of claim 8, wherein the [processor is further configured to block the users from querying, via their respective computing device, the plurality of datasets based on the generated access control permissions] *user policy provides restricted access for the one or more users of the organization to one or more of the datasets.*

13. The [system] *computer program product* of claim 8, wherein the [information policy further comprises at least one of a permission to explore meta-data, a permission to query data for aggregated results, a permission to query sensitive attributes, a permission to set protocol-based permissions, a permission to extract patient level data, and a permission to extract sensitive attributes] *user policy prevents the one or more users of the organization from access to one or more analytical tools to use on the datasets.*

14. The [system] *computer program product* of claim 8, wherein [each of the plurality of licenses comprises at least one of a permission to set a user account, a permission to set access restrictions, a permission to set access period, a permission to define refresh periods, a permission to define user limits, and a permission to define access tools] *the master policy defines access for one or more administrators to the datasets.*

15. A [method] *computer system connected to a network* to provide permissions for users from different organizations to access health information of cohort members while assuring privacy and security of the cohort members' health information [is] deposited in a plurality of datasets having different commercial owners who control the access to the datasets they own, [wherein the access is achieved via computing devices having a hardware processor communicatively connected to the plurality of datasets via a network, the method comprising the steps of] *the system comprising*:

*one or more processors configured to:*

[defining, by the processor,] *define* an information policy including permissions set by the different commercial owners of each of the plurality of datasets for access to [the health information and granularity of the health information in] each of the plurality of the datasets;

[an organization policy including permissions derived from a plurality of licenses subscribed to by the respective organizations for accessing each of the plurality of datasets;

a user policy including account permissions selectively assigned to the users from each of the different organizations;

generating] *generate* a master policy [having access control permissions for access to the plurality of datasets for each of the users from each of the different organizations, wherein the master policy comprises] *for one or more users of an organization based on* the information policy, *an* organization policy, and [the] *a* user policy;

[defining, by the processor, an administrator policy including permissions for control of the information policy, and the organization policy;] and

[in response to a request from the computing device of the users:

controlling, by the processor,] *control* access to [the] health information of [the] cohort members in the plurality of datasets based on the [access control permissions of the] master policy.

16. The [method] *system* of claim 15, [further comprising a step of blocking, by the processor, the users from querying, via their respective computing device, the plurality of datasets based on the generated access control permissions] *wherein the information policy includes access permissions to the datasets requested by one or more dataset owners*.

17. The [method] *system* of claim 15, wherein the [administrator policy,] *organization policy inherits permissions from* the information policy[, and the user policy have a hierarchical architecture].

*18. The system of claim 15, wherein the user policy includes one or more account permissions for each of the one or more users of the organization to access the datasets.*

*19. The system of claim 15, wherein the information policy and the organization policy have a hierarchical architecture.*

*20. The system of claim 15, wherein the master policy includes one or more access control permissions for the datasets.*

* * * * *